US00PP08213P

United States Patent [19]

Orton, Jr. et al.

[11] Patent Number: Plant 8,213

[45] Date of Patent: Apr. 27, 1993

[54] DOGWOOD TREE NAMED 'D-184-11'

[75] Inventors: Elwin R. Orton, Jr., Somerville; David A. Gant, Wall Township, Monmouth County, both of N.J.

[73] Assignee: Rutgers University, New Brunswick, N.J.

[21] Appl. No.: 740,637

[22] Filed: Aug. 5, 1991

[51] Int. Cl.[5] ..... A01H 5/00

[52] U.S. Cl. ..... Plt./53.2

[58] Field of Search ..... Plt./53.2

[56] References Cited

U.S. PATENT DOCUMENTS

PP. 7,732 12/1991 Orton ..... PLT 53.2

*Primary Examiner*—James R. Feyrer

*Attorney, Agent, or Firm*—Frank B. Robb

[57] ABSTRACT

The outstanding characteristics of the cultivar hereof comprise the white bracted display over a period of time typical of most plants of *C. florida*, an important distinguishing element of this new hybrid comprising the fruit which are bright red and much larger than the fruit typical for *C. florida* being nearly tubular or almost uniformly cylindrical in shape, the volume of the fruit being substantially greater than the volume of fruit of other cultivars, the vegetative and floral parts being winter-hardy in the region of New Brunswick, N.J.

2 Drawing Sheets

BACKGROUND OF THE INVENTION

The invention hereof is a controlled cross from what is generally known as a native eastern dogwood, perhaps better known as *Cornus florida* L.

This cultivar is a product of a long and careful program to develop dogwoods of various sizes, shapes and forms and appearance, as well as to overcome some of the problems which exist in dogwoods which diminish their commercial value. In particular there is disclosed an outstanding and colorful tree with a display more outstanding as compared with the usual and well known dogwood of the *C. florida* and other common varieties.

This program of hybridizing has extended over many, many years and has resulted in a number of valuable additions to the dogwood family.

The new dogwood was selected as a seedling from the progeny of a controlled cross involving an unnamed white-bracted seedling and an unnamed plant of *C. florida* var. rubra West, this having taken place in a cultivated area and as part of the program before noted.

As a result of the program, there are distinguishing characteristics which appear to be valuable. Our new cultivar is one which can be and has been asexually reproduced by us, by stem cuttings, and can be so reproduced by budding and/or grafting as may be most appropriate.

The area in which the plant hereof was developed and is currently existing, is that of New Brunswick, N.J., and for the trade the same will be known by the commercial name of 'D-184-11', the identifier which it was assigned when selected, and has for local identification, the synonym 'Rutman'.

DESCRIPTION OF THE INVENTION

In more specific terms, the dogwood hereof may be stated as being a medium-sized tree of upright, spreading form with horizontal branching typical of the species *C. florida*, however the new intraspecific hybrid exhibits unusually high vigor for plants of this species.

As will be setforth subsequently in a detailed description, the plant does in fact appear to have very decidedly distinctive characteristics which are valuable and provide for a commercial plant of considerable merit.

It should be noted that the tree is very floriferous and a regular bearer.

The flower buds themselves are large, nearly globose with rather flattened base. The white-bracted cultivars 'Cherokee Princess' and 'Springtime' have flower buds significantly smaller than those of 'D-184-11'.

The true flowers are tiny and relatively inconspicuous and are borne in dense heads, enclosed over winter by four involucral bracts that subtend the true flowers.

As has been suggested, one of the most important distinguishing characteristics of this particular plant is the fruit of this new hybrid which is a bright red fruit, much larger than the fruit typical for *C. florida* and is nearly tubular or almost uniformly cylindrical in shape as contrasted with smaller fruit with tapered ends that is typical of *C. florida*.

We have found the relative resistance or susceptibility of plants of this variety 'Rutman' to the various insect pests known to attack plants of *C. florida* is expected to be typical, but no long time information has been assembled as to its resistance throughout the United States.

As to disease, the relative resistance of plants of 'Rutman' to the diseases known to attack the plants of *C. florida* has not been broadly tested, but the original seedling of 'Rutman' has outgrown many older plants of other cultivars of *C. florida* in dogwood trials in the area of New Brunswick, N.J.

With the foregoing generally highlighted areas of description, a detailed analysis and descriptive elements of our new variety follows under the headings which are set forth.

The illustrations accompanying this description, show in FIG. 1 a typical plant of 'Rutman' as being 5.78 meters in height and 6.62 meters in width.

Figure 1:
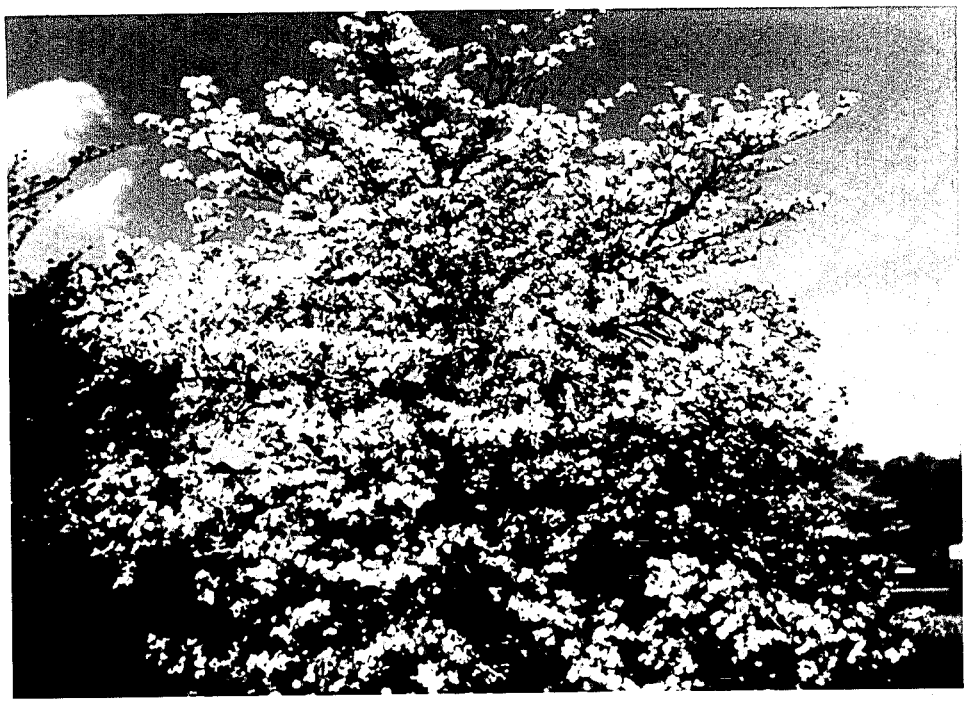
Figure 2:
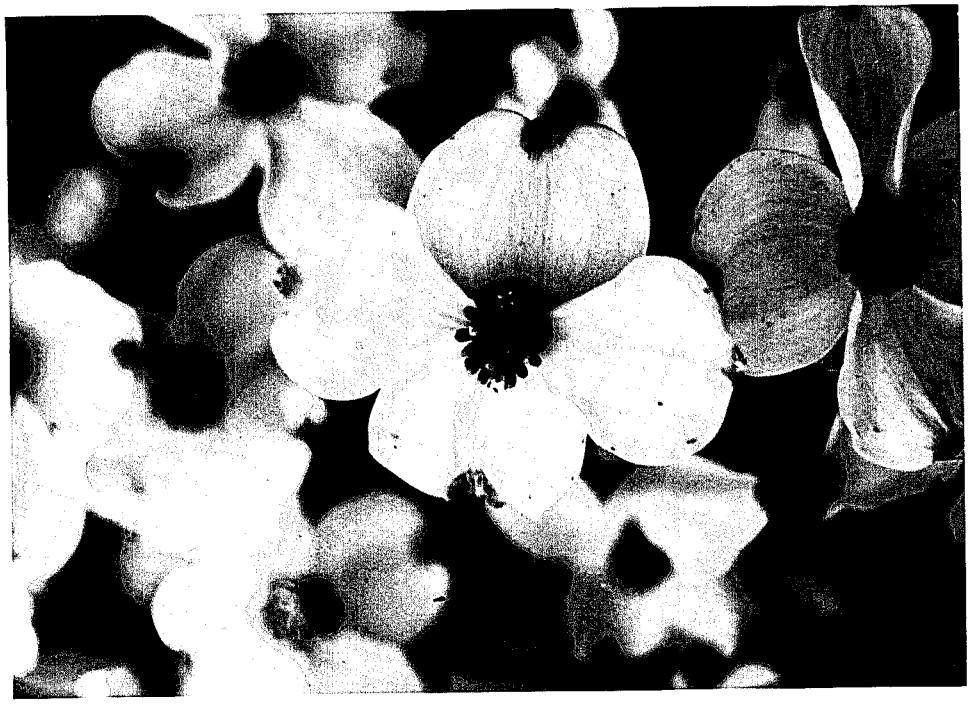
FIG. 2 shows the floral bracts with one being emphasized as fully expanded, diameter of the involucre from tip to tip of the opposing inner bracts being about 103.7 mm.
Figure 3:
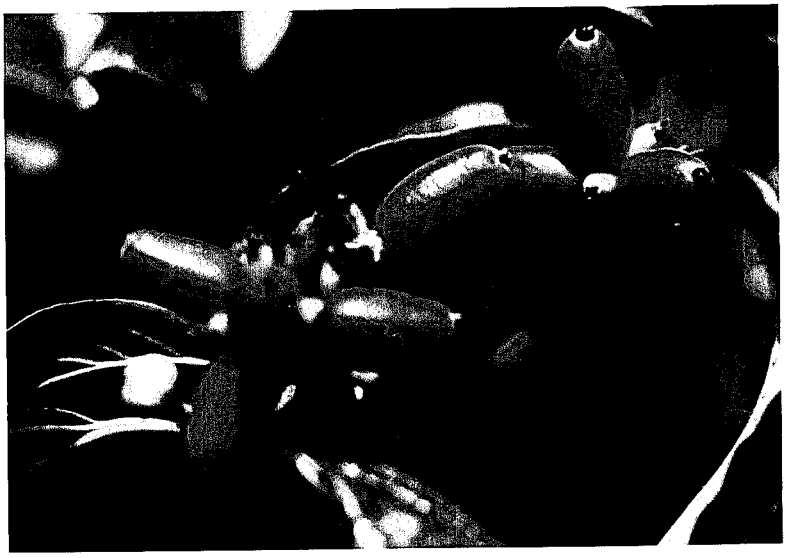
FIG. 3 shows the fruit of this cultivar which is an important characteristic hereof.

Where color is referred to hereinafter it is compared with *The R.H.S. Colour Chart* of The Royal Horticultural Society, London, the photos disclosing the colors in the best known manner as may be obtained from reproductions of this character.

DETAILED DESCRIPTION OF THE INVENTION

Propagation: Has been asexually reproduced by stem cuttings, by budding and/or grafting. Reproduction has taken place in the area of New Brunswick, N.J.

Classification:

*Botanic name.*—*Cornus florida* L.

*Commercial name.*—'D-184-11'.

Tree: Medium-sized tree of upright, spreading form with horizontal branching exhibiting unusually high vigor for plants of this species. After many years the original plant of 'D-184-11' was larger than plants of 'Sweetwater', 'Springtime', and 'Cherokee Princess' that were planted in dogwood trails as two-year grafted plants, some years before the original plant of 'D-184-11' appeared as a seedling. The original plant of 'D-184-11' measured 5.1 meters tall, 5.7 meters in width, whereas the best plant each of 'Cherokee Princess', 'Springtime', and 'Sweetwater' during the same trails measured respectively from two year grafts, 3.73 meters tall, 5.93 meters wide, 3.20 meters tall by 4.87 wide, and 4.26 meters tall by 5.17 meters wide. Vegetative and floral parts are fully winter-hardy in the area of New Brunswick, N.J. Plant Hardiness Zone — Zone 6 (0 degrees to −10 degrees F.). Very floriferous. Regular bearer.

Trunk: Smooth as a young plant, but bark becomes shaggy with age, typical for plant of *C. florida*. Color of trunk or bark is 197C (Greyed-Green Group) on The R.H.S. Colour Chart of The Royal Horticultural Society, London.

*Branches.*—Smooth, 197C (Greyed-Green Group) on The R.H.S. Colour Chart.

Leaves: Elliptical, with base broadly cuneate, sometimes mildly oblique, and tip abruptly acuminate.

*Length.*—8.5 to 14.6 cms.

*Width at widest point.*—5.1 to 8.2 cms.

*Petiole length range.*—1.2 to 3.2 cms.

*Color.*—Upper surface is 137A (Green Group); Lower surface is 138B (Green Group).

Flower buds: Large, nearly globose with rather flattened base. Width ranges from 7.5–10.5 mm. Height ranges from 6.75–9.0 mm. The white-bracted cultivars of 'Cherokee Prince' and 'Springtime' both have flower buds significantly smaller than those of 'D-184-11'. True flowers of this cultivar are tiny and relatively inconspicuous (each with four minute petals), are borne in dense heads, and are enclosed over winter by four involucral bracts that subtend the true flowers.

Involucral, or floral, bracts:

*Color when full expanded.*—Upper surface 155A (White Group); lower surface 155A to 155B (White Group). The outer 1–2 mm. of the tip of the lower surface of the floral bracts appears as a red blotch (55A, Red Group).

*Size and shape.*—When the floral bracts are fully expanded, the diameter of the involucre from tip to tip of the opposing inner bracts is about 103.7 mm.; the diameter of the involucre as measured from tip to tip of the opposing outer is approximately 90.5 mm. The average length of the inner and outer bracts is 49 mm. and 39 mm., respectively. The width of the inner and outer bracts at their widest point is about 43.2 mm. and 44.3 mm., respectively. Length and width of the floral bracts can vary considerably from year to year, but the inner bracts mostly likely will be clearly longer and very slightly more narrow than the outer bracts in any given year. The outer bracts are rounded and very broadly tapered at the base, whereas the inner bracts are more nearly obovate, being more acutely tapered at the base. All of the bracts exhibit an emarginate tip.

*Peduncle length.*—Each flower head is borne on a peduncle, the average length of which is about 26 mm. at the time of flowering and/or floral (bracts) display. The absolute peduncle length will vary somewhat from year to year.

*Flowering and floral display.*—The period of floral display (floral bracts) is typical of that for most plants of *C. florida;* i.e., occurring in late April and early May in the vicinity of New Brunswick, N.J., and extending for a period of 10–15 days, depending on weather conditions. Anthesis of the tiny, relatively inconspicuous, true flowers commences two or four days after the onset of the ornamental display of the large floral bracts and continues for about seven to ten days, depending on weather conditions. The average number of true flowers per flower head in our new, intraspecific hybrid is about 27.23, which is about the same as that found with the cultivars 'Cherokee Princess' and 'Springtime'.

*Fruit.*—The bright, red fruit (46B, Red Group) are much larger than the fruit typical for *C. florida* and are nearly tubular, almost uniformly cylindrical in shape.

Resistance to:

*Insects.*—As to the relative resistance or susceptibility of plants of 'D-184-11' to the various insect pests known to attack plants of most cultivars of *C. florida* little information is available as the plants of 'D-184-11' have not been widely tested throughout the United States.

*Diseases.*—The relative resistance or susceptibility, of plants of 'D-184-11' to the various disease organisms known to attack plants of *C. florida* has not been thoroughly tested but, as stated above, the original seedling of 'D-184-11' has outgrown many older plants of other cultivars of *C. florida* in dogwood trails at Rutgers University.

We claim:

1. A new and distinct cultivar of dogwood tree, substantially as herein shown and described, characterized particularly as to novelty by the unique combination of its unusually vigorous growth, large floral buds, extremely large, tubular bright red fruit, winter hardiness, and tree size being substantially larger than some other varieties.

* * * * *